(12) United States Patent
Borras Cuesta et al.

(10) Patent No.: US 7,582,609 B2
(45) Date of Patent: Sep. 1, 2009

(54) METHOD FOR THE TREATMENT OF SKIN FIBROSIS AND SUITABLE COMPOSITIONS FOR SUCH TREATMENT

(75) Inventors: Francisco Borras Cuesta, Pamplona (ES); Javier Dotor De Las Herrerias, Pamplona (ES); Juan Manuel Irache Garreta, Pamplona (ES); Fernando Martinez Galan, Pamplona (ES); Jesus Prieto Valtuena, Pamplona (ES)

(73) Assignee: Digna Biotech, S.L., Navarra (ES)

( * ) Notice: Subject to any disclaimer, the term of this patent is extended or adjusted under 35 U.S.C. 154(b) by 0 days.

(21) Appl. No.: 11/365,764

(22) Filed: Mar. 1, 2006

(65) Prior Publication Data
US 2007/0207965 A1    Sep. 6, 2007

(51) Int. Cl.
*A61K 9/107* (2006.01)
*A61K 38/08* (2006.01)
*A61K 38/10* (2006.01)

(52) U.S. Cl. ............... 514/14; 514/15; 514/16; 514/17; 514/937

(58) Field of Classification Search ............... None
See application file for complete search history.

(56) References Cited

U.S. PATENT DOCUMENTS

| 5,650,494 | A | 7/1997 | Cerletti et al. |
| 7,057,013 | B1* | 6/2006 | Saenz et al. ............ 530/326 |
| 2003/0138505 | A1* | 7/2003 | Fischer et al. ............ 424/744 |
| 2005/0095261 | A1* | 5/2005 | Popp ............ 424/400 |
| 2006/0233708 | A1* | 10/2006 | Huang ............ 424/1.69 |

FOREIGN PATENT DOCUMENTS

| FR | 2 720 069 | 11/1995 |
| WO | 92/20793 | 11/1992 |
| WO | 96/25178 | 8/1996 |
| WO | 00/31135 | 6/2000 |

OTHER PUBLICATIONS

Santiago et al. Topical Application of a Peptide Inhibitor of Transforming Growth Factor Beta-1 . . . Journal of Investigative Dermatology. Sep. 2005, vol. 125, pp. 450-455.*
Ezquerro et al. A synthetic peptide from transforming growth factor beta type III receptor . . . Cytokine. 2003, vol. 22, pp. 12-20.*
English Translation of WO 00/31135 dated Jun. 2, 2000.
English Abstract of FR 2 720 069 dated Nov. 24, 1995.
Skolnick, J., et al. "From genes to protein structure and function: novel applications of computational approaches in the genomic era." *Trends in Biotech* (2000) vol. 18, pp. 34-39.
Attwood, T. K. "The Babel of Bioinformatics." *Science* (2000) vol. 290 pp. 471-473.
Metzler, W. J., et al. "Solution structure of human CTLA-4 and delineation of a CD80/CD86 binding site conserved in CD28." *Nature Structural Biology*, (1997) vol. 4, No. 7 pp. 527-531.

* cited by examiner

*Primary Examiner*—Jeffrey E Russel
(74) *Attorney, Agent, or Firm*—Ladas and Parry LLP

(57) ABSTRACT

A Method for the treatment of skin fibrosis with a peptide that inhibits TGF-β, and suitable compositions for its administration. The method includes in particular, the use of peptide P144, a compound that is a known inhibitor of TGF-β, for the treatment of skin fibrosis by topical application. The method is shown effective in an animal model of bleomycin-induced skin sclerosis, to a reduction both of the skin fibrosis and of the content of soluble collagen, without any signs of systemic toxicity being detected. This shows that P144 is effective for topical application in mammals for treating fibrotic skin diseases and pathological scarring of the skin. For the administration of this peptide, stable compositions are also supplied, with pleasant appearance without being greasy, with good spreading characteristics and with a viscosity that permits it to be processed easily in industrial plant, and which are suitable for administering the peptide to humans.

14 Claims, 9 Drawing Sheets

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial
<220> FEATURE:
<223> OTHER INFORMATION: Obtained from the modified type III human TGF beta 1 receptor,
      positions 730-743
<220> FEATURE:
<221> NAME/KEY: Peptide
<222> LOCATION: (1)..(14)

<400> SEQUENCE: 1

Thr Ser Leu Asp Ala Ser Ile Ile Trp Ala Met Met Gln Asn
1               5                   10

<210> SEQ ID NO 2
<211> LENGTH: 12
<212> TYPE: PRT
<213> ORGANISM: Artificial
<220> FEATURE:
<223> OTHER INFORMATION: Obtained from the type III rat TGBeta 1 receptor, positions
      731-742
<220> FEATURE:
<221> NAME/KEY: peptide
<222> LOCATION: (1)..(12)

<400> SEQUENCE: 2

Thr Ser Leu Asp Ala Thr Met Ile Trp Thr Met Met
1               5                   10
```

US 7,582,609 B2

METHOD FOR THE TREATMENT OF SKIN FIBROSIS AND SUITABLE COMPOSITIONS FOR SUCH TREATMENT

FIELD OF THE INVENTION

The invention relates to the treatment of skin fibrosis by topical application of inhibitors of TGF-β. More particularly, the invention relates to the use of Peptide P144, an inhibitor of TGF-β, for the treatment of skin fibrosis by its topical application, as well as to compositions that contain said peptide suitable for application to human beings by the topical route.

BACKGROUND OF THE INVENTION

Excessive accumulation of extracellular matrix (ECM) proteins is the distinctive feature of fibrotic skin conditions such as hypertrophic scars keloids and localized or systemic sclerosis (scleroderma). This process is dependent on activation of the synthesis of ECM in interstitial fibroblasts, which are often transformed to myofibroblasts that are positive for smooth muscle α-actin (alpha smooth-muscle actin, α-SMA), a marker that is indicative of differentiation to cells with a high rate of proliferation and production of extracellular matrix (Jiménez et al., 1996; Jelaska and Korn, 2000).

One of the key molecular factors in fibrotic processes is transforming growth factor β (TGF-β), which is overexpressed in the majority of fibrotic diseases and displays various profibrotic effects in fibroblasts (Querfeld et al., 1999; Chiller et al., 2004). Activation of the TGF-β receptors leads to the activation of various kinase signalling cascades, leading to phosphorylation of SMAD proteins, as well as to the activation of SMAD-independent kinases, which together activate the synthesis of ECM and the growth of fibroblasts and differentiation to give rise to myofibroblasts (Shi and Massague, 2003; Daniels et al., 2004).

Connective-tissue growth factor (CTGF), for its part, is a soluble mediator that is induced rapidly and selectively in the fibroblasts by the action of TGF-β (Leask et al., 2004). CTGF has also been detected specifically in fibrotic skin diseases (Igarashi et al., 1996) and, in animal models, promotes and perpetuates the profibrotic effects of TGF-β (Frazier et al., 1996). Although the role of epidermal CTGF in fibrosis has not been well established, earlier studies show that it is expressed by normal keratinocytes in vivo (Quan et al. 2002) and that the negative regulation of its levels caused by ultraviolet radiation appears to be linked to reduction in the synthesis of procollagen induced by said radiation (Quan et al., 2002).

Although the majority of fibrotic diseases usually start with variable degrees of inflammation, anti-inflammatory treatments are not effective when used in the treatment of chronic fibrotic diseases, which represent an important group of lesions for which there is no specific treatment. TGF-β appears to be an attractive target for the treatment of fibrotic diseases; in fact, various anti-TGF-β strategies have been tried successfully in animal models for fibrosis, including various murine models of scleroderma (MacCormick et al., 1999; Yamamoto et al., 1999b; Zhang et al., 2003; Lakos et al., 2004). In the animal model of bleomycin-induced cutaneous sclerosis (a model that reproduces most of the characteristics of human scleroderma, such as infiltration of the skin with inflammatory cells, vascular damage, activation of mast cells and prolonged skin fibrosis (Yamamoto et al., 1999c), previous studies showed that both the administration of anti-TGF-β antibodies and genetic deficiency of SMAD3 inhibit the development of fibrosis, which lends strong support for a fundamental role of TGF-β (Yamamoto et al., 1999b; Lakos et al., 2004) in the genesis and development of sclerosis. In studies using the animal model of bleomycin-induced scleroderma, systemic treatment with anti-TGF-β antibodies reduces fibrosis in parallel with a reduction in mast cells and in infiltration of inflammatory cells (Yamamoto et al., 1999b). The relevance of the mast cells in the models of skin fibrosis is uncertain, because earlier studies in mastocyte-deficient mice demonstrated that their contribution to the development of fibrosis is not indispensable (Everett et al., 1995; Yamamoto et al., 2001). For its part, infiltration of inflammatory cells plays an important role in the early stages of development of fibrosis, but its role is less clear in the later stages, in which it may disappear or persist independently of the progression of the fibrosis, but usually fibrosis progresses in the absence of significant infiltration of inflammatory cells.

Despite these encouraging results, inhibition of TGF-β by the systemic route is a cause of disquiet regarding its safety, because this factor triggers powerful pleiotropic effects in immunomodulation, inflammation and in the development of tumours (Akhurst, 2002). In keeping with this, in mice deficient in TGF-β1, the formation of scars on the skin was reduced, but the animals developed cachectic syndrome (characterized by pronounced weight loss), accompanied by a generalized inflammatory response and tissue necrosis, resulting in organ failure and death (Bottinger et al., 1997). Therefore local instead of systemic inhibition of TGF-β represents an alternative strategy for the development of antifibrotic treatments (Daniels et al., 2004; Lakos et al., 2004). Local inhibition of TGF-β had been tried before, by direct application of neutralizing antibodies on open wounds on the skin or the cornea, but the application of antibodies or of large peptides with the intention that they should cross the epidermal barrier was not found to be a very practical strategy (Jester et al., 1997; Brahmatewari et al., 2000), as these molecules are too large and their diffusion through the epidermal barrier is hampered.

It would be interesting to find a compound with sufficient capacity to diffuse through the epidermal barrier, capable of inhibiting TGF-β when administered locally, and with a capacity for curing or ameliorating the effects of skin fibrosis in mammals. Moreover, if said molecule is really to be useful for the treatment of humans, it would be necessary to develop a pharmaceutical form suitable for topical administration of said active compound, which not only would permit local action of the compound without being absorbed significantly, but would display good spreading capacity and a pleasant appearance without being greasy.

These requirements are met by the novel use of peptides, including peptides that are already known, including in particular the peptide designated P144, whose use is described in the present invention for the treatment of skin fibrosis by its topical application, compositions also being supplied which contain said peptide and are suitable for topical administration for humans. Peptide P144, described in international patent application WO 00/31135, is an antagonist of TGF-β1 which comprises the amino acids 730 to 743 of the type III receptor (β-glycan) of human TGF-β1 (accession number Q03167, SwissProt) and had been demonstrated in vitro to be capable of interfering with the binding of TGF-β1 to its cellular receptors in Mv-1-Lu cells and preventing the inhibition of proliferation of said cells induced by TGF-β1. Conversely, when administered intraperitoneally it gives rise to a powerful antifibrotic response in the liver of rats, in which liver cirrhosis is induced by inhalation of carbon tetrachloride. However, its topical administration, as well as its possible usefulness in the treatment of established skin fibrosis, had not heretofore been described. Compositions suitable for the topical administration of said peptide had not been described either; this need is also covered by the present invention.

SUMMARY OF THE INVENTION

The invention relates to the use of a peptide for the manufacture of a medicinal product for the prevention and treatment of skin fibrosis by its topical administration. In a preferred embodiment of the invention, the peptide is an inhibitory peptide of TGFβ1 having 6 to 20 amino acids (preferably 12 to 16) wherein said peptide has been selected from the group consisting of:
- i) a fragment of P144 (SEQ ID NO: 1) or P54 (SEQ ID NO: 2) with at least 6 amino acids;
- ii) a peptide that comprises at least six consecutive amino acids from peptide P144 or P54; and
- iii) a peptide having more than 75% homology (preferably more than 80%, more preferably more than 90%) with the amino acid sequence of P144 or P54;

and wherein said peptide has
- a) a molecular weight ranging from 700 to 3,000 Daltons; and
- b) a solubility value in a range from 3 to −9.

As used herein, the solubility value is obtained from the total addition of each amino acid score according to the solubility valuation described in Hopp & Woods, (Hopp et al., 1981), the contents of which publications are hereby incorporated herein by reference. Negative values imply hydrophobicity and positive values imply that the amino acid is hydrophilic. The Hopp & Woods scale for a peptide with N amino acids, ranges from +Nx3 to −Nx3.

For purposes of the present invention, the degree of homology between two amino acid sequences is determined by using GAP version 8 from the GCG package (Genetics Computer Group, 575 Science Drive, Madison, Wis. 53711, USA) with standard penalties for proteins: GAP weight 3.00, length weight 0.100, Matrix described in Gribskov and Brugess, Nucl. Acids Res. 14(16); 6745-006763 (1986), the contents of which are hereby incorporated herein by reference.

In a most preferred embodiment, the peptide comprises the amino acids 730 to 743 of the type III receptor (β-glycan) of human TGF-β1 and whose capacity for acting as an inhibitor of human TGF-β1 had been demonstrated previously. It is a small peptide, whose sequence: TSLDASIIWAMMQN (SEQ ID NO: 1), moreover, endows it with a highly lipophilic character. These two characteristics permit its local use by topical application in the form of emulsion for the treatment of fibrotic skin diseases, with a reduction in the potential effects that might be triggered by the systemic administration of a TGF inhibitor.

As described later in the present specification, topical administration of an emulsion containing P144, to an animal model of bleomycin-induced cutaneous sclerosis leads to a reduction of skin fibrosis and of the content of soluble collagen, without signs of systemic toxicity appearing, as were revealed by studies of necrosis in mice treated for four weeks. Even if the bleomycin dose is increased tenfold, the simultaneous topical administration of peptide P144 is able to produce a significant decrease in thickness of the dermis relative to that observed in mice treated with bleomycin which were administered a P144-free emulsion topically. Furthermore, in mice with established fibrosis, topical treatment with P144-containing emulsion for two weeks following establishment of fibrosis significantly reduces skin fibrosis and the content of soluble collagen. These results show that P144 is a suitable compound for use in mammals for treating, by topical application of said peptide, pathological scarring of the skin, fibrotic skin lesions and, in general, any disease that has, as a consequence or complication, in a severe state, a varying degree of skin fibrosis.

The following are examples of diseases or lesions in which the peptides of the invention could be useful: keloids, hypertrophic scars (such as those resulting from surgery or injury), chemical burns or thermal burns (caused by heat or by cold), skin fibrosis associated with bone marrow transplantation, morphea, scleroderma and similar diseases (acrokeratoelastoidosis; atrophoderma of Pasini and Pierini; CREST syndrome; dermatitis artefacta; diffuse scleroderma; eosinophilic fasciitis; graft-versus-host disease; keloid scleroderma; lichen sclerosus; linear scleroderma; limited systemic scleroderma; mandibuloacral dysplasia; skin changes associated with myeloma; nephrogenic fibrosing dermopathy; overlap syndrome; Parry-Romberg syndrome; porphyria cutanea tarda; progeria; skin changes of polyneuropathy syndrome, organomegaly, endocrinopathy, monoclonal proteins and skin changes or POEMS; pseudoscleroderma; Buschke scleroderma; scleromyxoedema; vitiligo; Werner syndrome), acne, cellulitis, Dupuytren syndrome, Peyronie disease, wrinkles and, in general, any skin lesion or pathology that passes through a stage with fibrosis or increase in the production and/or activation of TGF-β, as well as any disease with skin fibrosis as a complication.

The invention also relates to compositions for the topical administration of the peptides, and preferably P144, in particular those having characteristics that make them suitable for use in the treatment of humans and that facilitate their handling during their manufacture and packaging. The following are regarded as suitable characteristics:
- Pleasant appearance without being greasy
- Good spreadability
- Stability as emulsion over a prolonged period, sufficient to guarantee its stability during storage prior to use
- A composition of the semi-solid form that permits its handling in machinery and, thus, its large scale production and dosage in the desired presentations.
- Permitting local action of the peptide without significant systemic absorption of said peptide In accordance with preferred embodiments of the invention, there are provided in Table 1, below, further preferred formulations of the compositions for use with the invention, including generic descriptions of compounds used in the composition, the functions thereof and the preferred, more preferred and most preferred ranges for these compounds.

TABLE 1

| Component | Group | Function | Desired | Preferred | More preferred |
|---|---|---|---|---|---|
| Dimethicone 350 | Silicones (Dimethicone n: 250-400) | Emollient and antifoaming | 0.5 to 30% | 9 to 12% | 9.0 to 11.0% |

TABLE 1-continued

| Component | Group | Function | Desired | Preferred | More preferred |
|---|---|---|---|---|---|
| Liquid paraffin | Mineral oil | Emollient, oleaginous vehicle, lubricant | 1 to 45% | 32 to 45% | 40 to 45% |
| Cetrimide | Cationic Surfactant | Emulsifier, antimicrobial | 0.1 to 3% | 0.5 to 1% | 0.25 to 0.75% |
| Methylparaben | Parabens (Antimicrobial preservative) | Antimicrobial | 0.0 to 0.3% | 0.02 to 0.04% | 0.02% |
| Propylparaben | Parabens (Antimicrobial preservative) | Antimicrobial | 0.0 to 0.6% | 0.01 to 0.03% | 0.01% |
| Chlorocresol | Antimicrobial preservative | Antimicrobial | 0.0 to 0.2% | 0.05 to 0.2% | — |
| Cetostearylic alcohol | Emollient, emulsifying agent, viscosity-increasing agent | Viscosity-increasing agent | 0.5 to 50% | 0.5 to 3.0% | 1.5% |
| Dymethylsulphoxide (DMSO)* | Organic solvent | Cosolvent | 0.1 to 5% | 0.1 to 0.5% | 0.1 to 0.3% |
| Peptide P144 | | Bioactive compound | 0.001 to 0.035% | 0.005 to 0.035% | 0.01 to 0.03% |
| Purified water | | vehicle | Balance | Balance | Balance |

*Weight/volume ratio (w/v)

The antimicrobial agents may be a mixture of methyl propyl or, alternatively, chlorocresol.

The methods of treatment of skin fibrosis in which the peptide is administered topically or topical compositions that contain said peptide constitute an additional aspect of the invention.

Although the present description focuses on the peptides described above, and in particular peptide P144, the compound to be used for the treatment of skin fibrosis by its topical administration could be any of the other TGF-β1 inhibitor peptides described in U.S. patent application Ser. No. 09/831,253, filed on 23 Nov. 1999, the contents of which are hereby incorporated herein by reference. Accordingly, the scope of the present invention also includes the use of any of said peptides for the manufacture of a medicinal product for the treatment of skin fibrosis by its topical administration, as well as any method of treatment of skin fibrosis in which any of said peptides is administered topically.

The invention will now be described in more detail by means of the Drawings and the Examples that are presented below.

a-TGF: mice injected with bleomycin for 4 weeks with simultaneous topical application of an emulsion containing peptide P144; VEHIC: mice injected with bleomycin for 4 weeks with simultaneous topical application of an emulsion that only contained the vehicle for administration. *: p<0.05.

Figure 4:
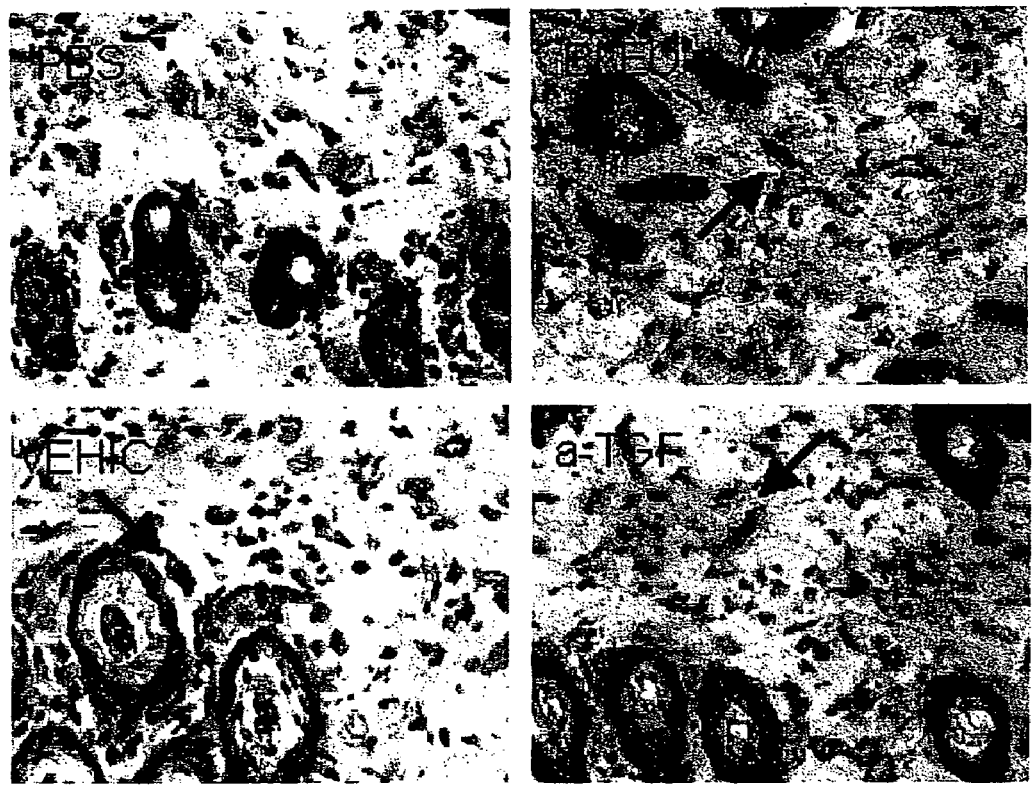
Figure 4:
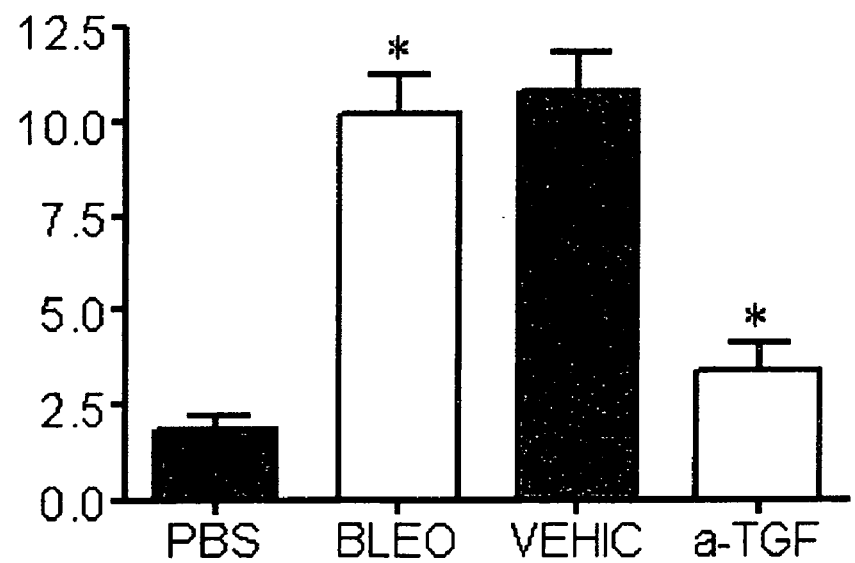

FIG. 4 corresponds to the immunohistochemical detection of phospho-SMAD2/3 in skin sections from mice used in tests for evaluating the effect of topical application of P144 on bleomycin-induced skin sclerosis. The photographs in part A correspond to sections labelled with an anti-phospho-SMAD2/3 antibody, the presence of which was revealed by using diaminobenzidine (brown), and contrast staining with haematoxylin. The presence of labelled fibroblasts is indicated with arrows. |Part B in the figure gives a graph showing the mean value±standard deviation of the number of cells positive for phospho-SMAD2/3 present per field in each of the samples. Samples: PBS: mice that were injected with PBS for 4 weeks; BLEO: mice that were injected with bleomycin for 4 weeks, without any composition being applied topically; a-TGF: mice injected with bleomycin for 4 weeks with simultaneous topical application of an emulsion containing peptide P144; VEHIC: mice that were injected with bleomycin for 4 weeks with simultaneous topical application of an emulsion that only contained the vehicle for administration. *: p<0.05.

Figure 5:
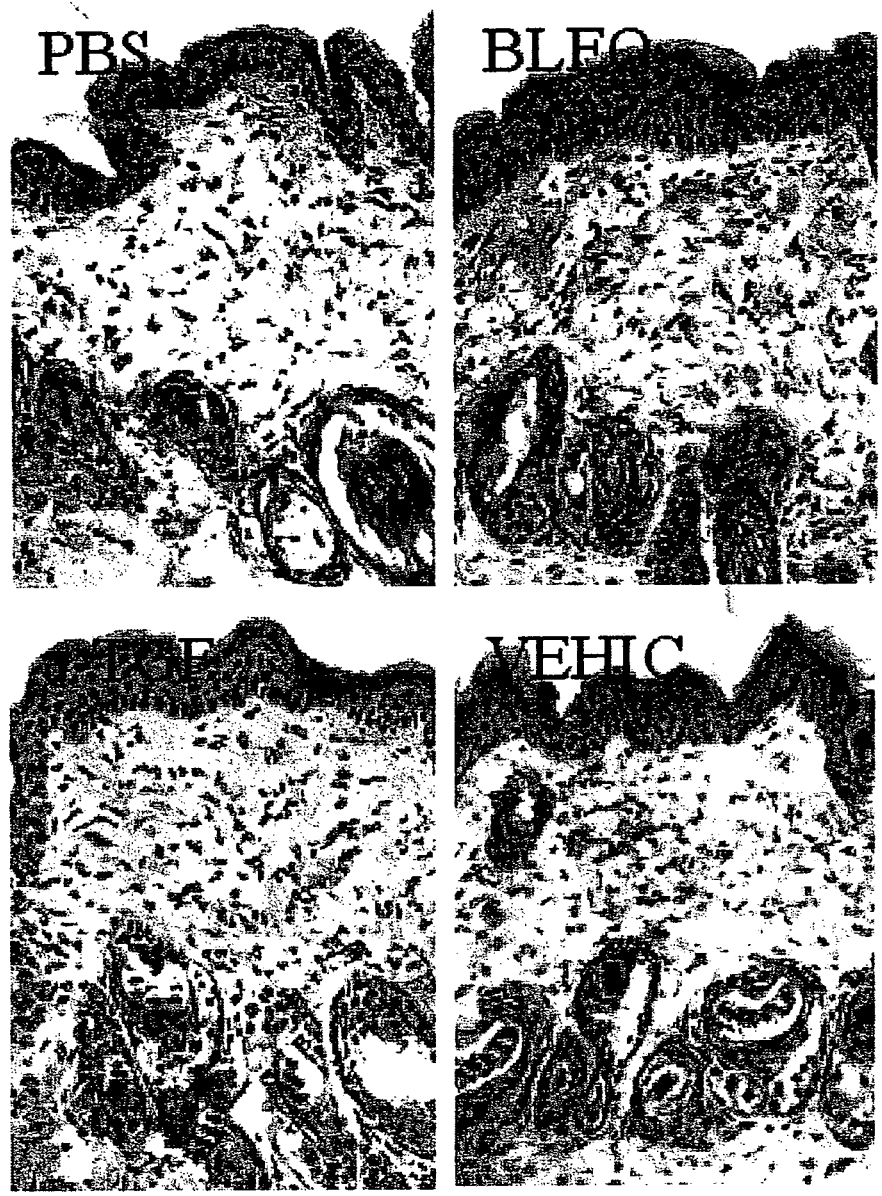

FIG. 5 corresponds to immunohistochemical detection of connective tissue growth factor (CTGF) in skin sections from mice used in tests for evaluating the effect of topical application of P144. The photographs correspond to sections labelled with an anti-CTGF antibody whose presence was revealed by using diaminobenzidine (brown), using contrast staining with haematoxylin. Samples: PBS: mice that were injected with PBS for 4 weeks; BLEO: mice injected with bleomycin for 4 weeks, without any composition being applied topically; a-TGF: mice injected with bleomycin for 4 weeks with simultaneous topical application of an emulsion containing peptide P144; VEHIC: mice injected with bleomycin for 4 weeks with simultaneous topical application of an emulsion that only contained the vehicle for administration.

Figure 6:
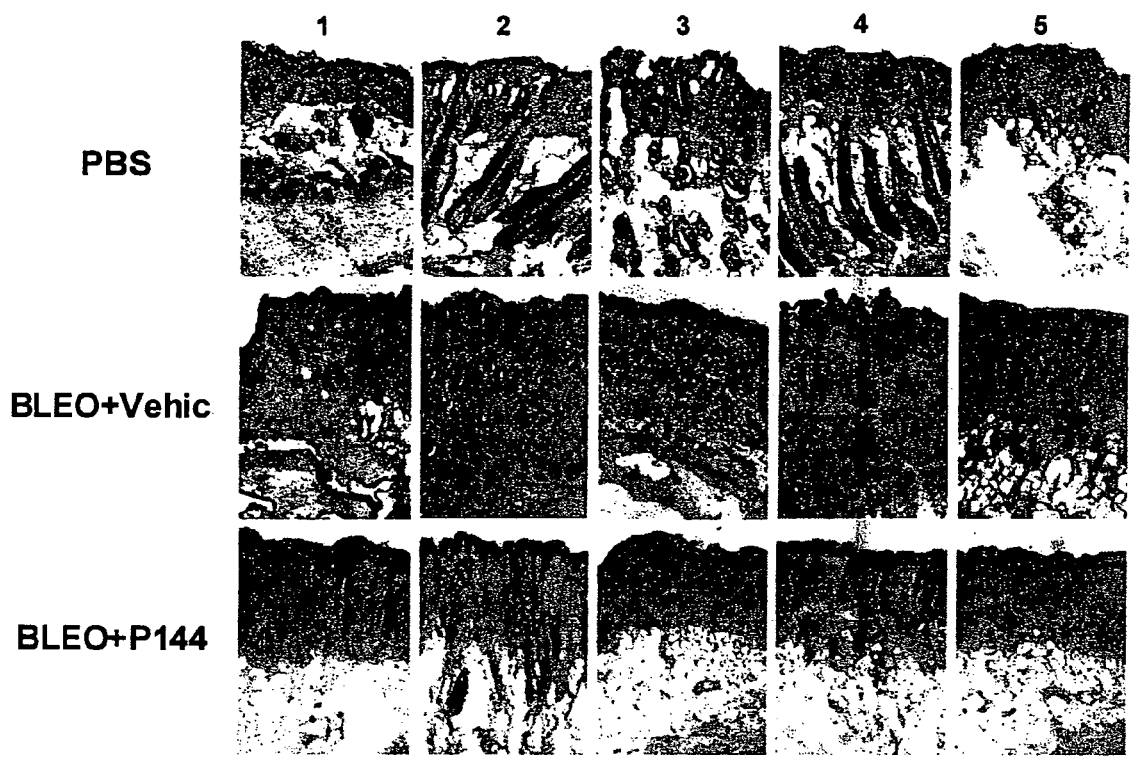

FIG. 6 shows staining, with haematoxylin-eosin, of subcutaneous sections from mice used in tests for histopathological evaluation of the effect of topical application of P144 on skin sclerosis induced by high concentrations of bleomycin. The photographs in the top row (labelled "PBS") correspond to mice that only received PBS in the injections and did not receive any composition by topical administration; the photographs in the middle row (labelled "BLEO+Vehic") correspond to mice that were injected with bleomycin and received, by topical application, an emulsion that only contained the vehicle for administration, during the period of administration of injections; the photographs in the bottom row correspond to mice that are injected with bleomycin and received, by topical application, an emulsion containing peptide P144, during the period of administration of injections. Magnification of the images: ×200. Each image is representative of one of the mice (1, 2, 3, 4, 5) in the various groups.

Figure 7:
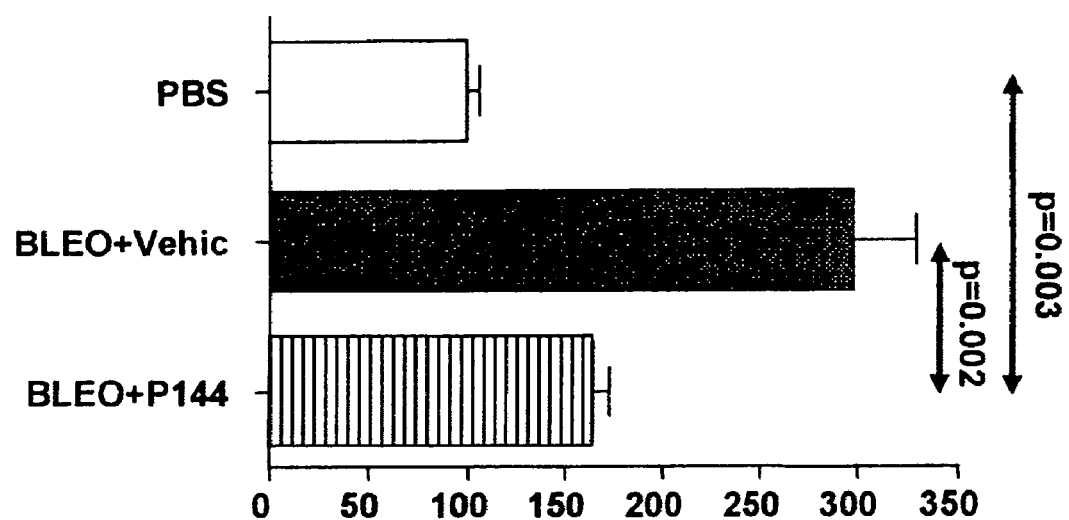

FIG. 7 shows a graph evaluating the effect of administration of an emulsion containing peptide P144 on the thickness of the dermis in mice treated with high doses of bleomycin. The values shown correspond to the mean±standard deviation of the percentage relative to the values found in the mice treated with PBS, adjusted to 100%. Each of the bars corresponds to the following treatments: unfilled bar (labelled "PBS"): mice injected with PBS for 4 weeks; bars with dark shading ■ (labelled "BLEO+Vehic": mice injected with high doses of bleomycin for 4 weeks, and with topical application of an emulsion containing only the vehicle for administration, during the same period; bar filled with vertical lines ∥ (labelled "BLEO-P144"): mice that were injected with high doses of bleomycin for 4 weeks, and topical application of an emulsion containing P144 during the same period.

Figure 8:
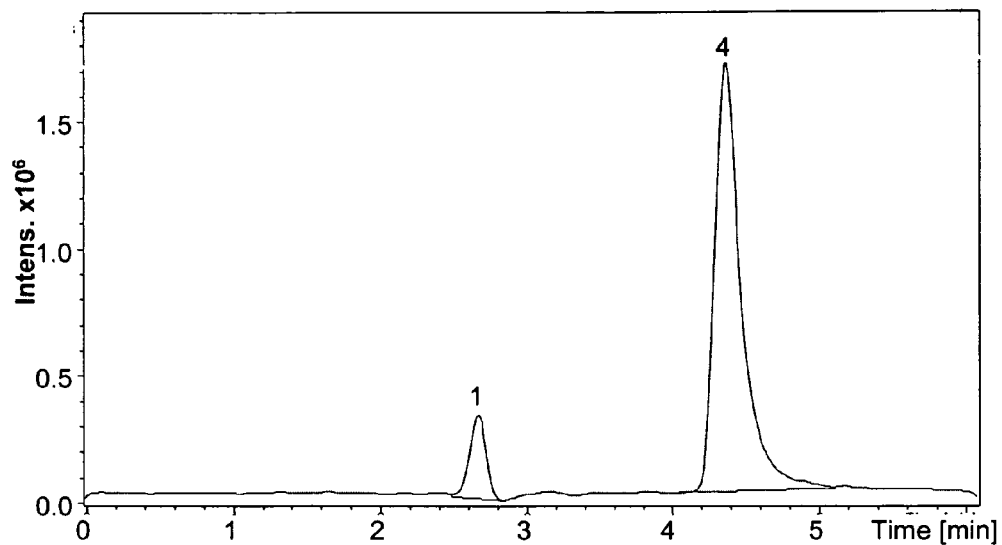

FIG. 8 shows a chromatogram corresponding to the analysis of P144 in an aqueous solution with 0.1% of trifluoroacetic acid, at a concentration of 100 ng/ml.

Figure 9:
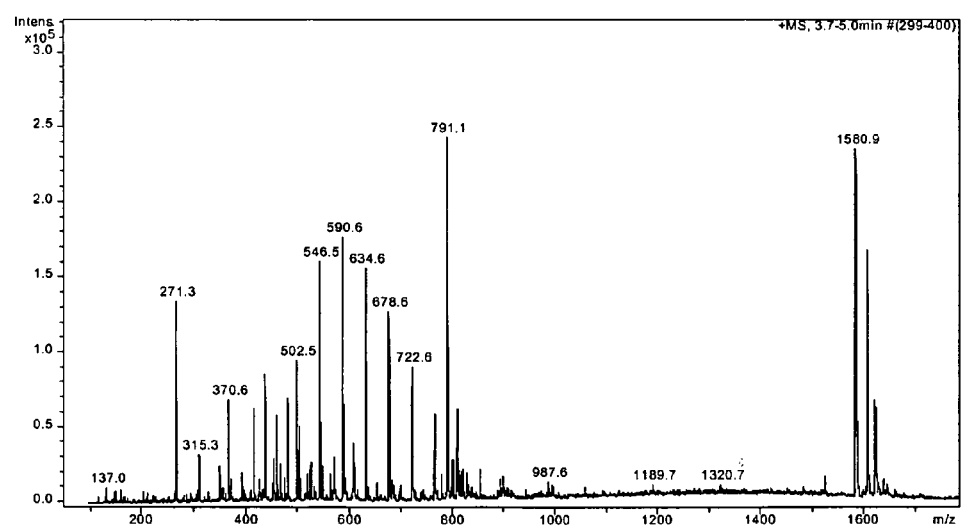

FIG. 9 shows the mass spectrum of peptide P144 obtained after analysis of a sample with a concentration of 1000 ng/ml of peptide P144.

Figure 10:
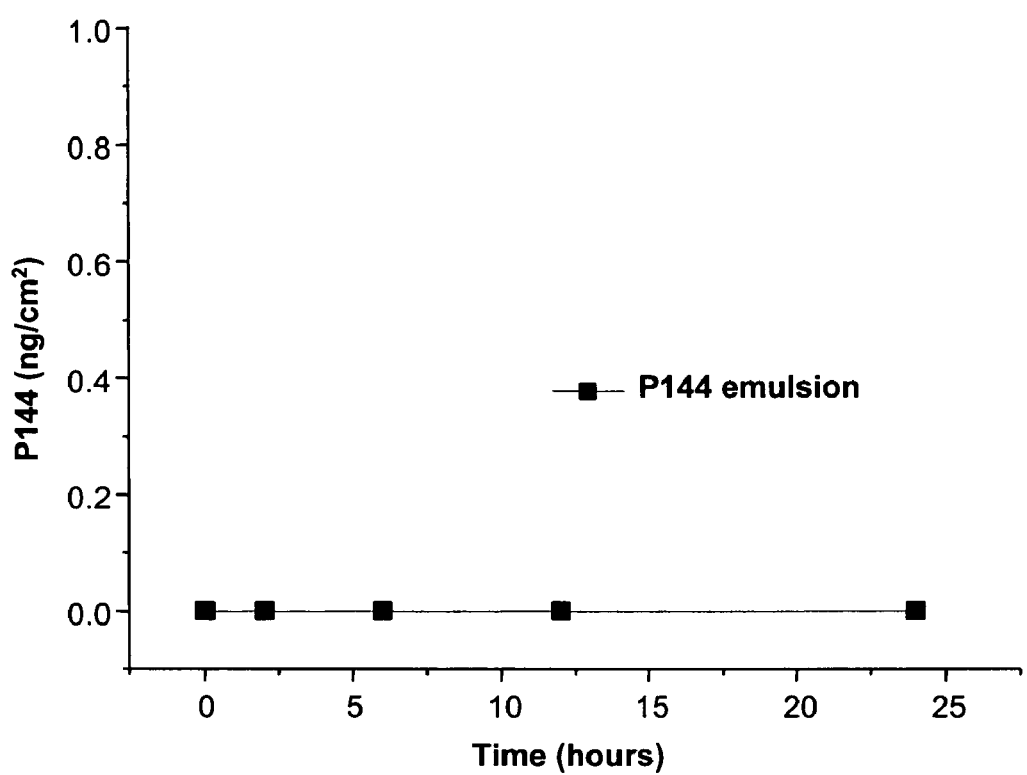

FIG. 10 shows the evolution of accumulated amount of peptide P144 in the receptor compartment of a Franz diffusion cell system's cell, that has been capable of crossing the 1-mm dermatomized pig skin membrane as a function of the time elapsed, when formulated in a semisolid emulsion (P144 emulsion). Peptide P144 (ng/cm$^2$); Symbols represent the mean SD; n=6.

DETAILED DESCRIPTION

As used herein, "consisting essentially of" means that the composition, component or peptide may include additional ingredients or amino acids, but only if the additional ingredients or amino acids do not materially alter the basic and novel characteristics of the claimed compositions or methods.

The following examples describe tests that were designed to test the antifibrotic effect of P144 in the animal model of bleomycin-induced skin sclerosis by using compositions in the form of an emulsion containing said peptide, and tests with variation of the basic formulation used for forming said emulsion to give a formulation that displays characteristics making it suitable for topical administration to humans and that could be manufactured on a large scale and dosed in commercial forms of preparation simply and efficiently. The compositions used in said tests were obtained using the products shown below in Table 2, which also shows the initial phase in which they were incorporated (aqueous or oily), before the two were combined to form an emulsion:

TABLE 2

Products used for production of the compositions used in the Examples

| Product | Manufacturer | Reference | Initial phase |
| --- | --- | --- | --- |
| Dimethicone 350 | Roig-Farma | 301119-09 | Oily |
| Paraffin | Roig-Farma | 31629-09 | Oily |
| Methylparaben | Roig-Farma | 31169-24 | Aqueous |
| Propylparaben | Roig-Farma | 31171-24 | Aqueous |
| Chlorocresol | Roig-Farma | 30432 | Oily |
| Cetrimide | Roig-Farma | 30414 | Aqueous |
| Cetostearyl alcohol | Roig-Farma | 30410-12 | Oily |
| Tween 80 | Roig-Farma | 31620-12 | Aqueous |
| Sodium laurylsulphate | Roig-Farma | 31037-27 | Aqueous |
| Stringy vaseline | Roig-Farma | 31628-09 | Oily |
| Aristoflex AVC | Clariant | 138240 | Oily |
| DMSO | Sigma | D-2650 | Aqueous |
| Peptide P144 | Sigma-Genosys | 39797-1 | Aqueous (together with DMSO) |
| Purified water | | | Aqueous |

The peptide P144 supplied by Sigma-Genosys, Ltd. (Cambridge, United Kingdom) had a purity of at least 90% according to the data from high-performance liquid chromatography and mass spectrometry.

The various emulsions were prepared according to the following production procedure:

Weigh the components of each phase of the emulsion (oily and aqueous phases) separately in stainless steel vessels of suitable capacity.

Heat the two phases separately on a bath with thermostatic control at 70° C. The vessel containing the aqueous phase must be covered to prevent losses by evaporation.

After approximately 20 minutes, the oily phase has melted and is homogeneous. Both phases must have a clear, homogeneous appearance with temperature of approximately 70° C.

Stirring the oily phase with a propeller stirrer (speed=3.5. IKA RW16 basic stirrer), pour the aqueous phase onto the oily phase a little at a time. This operation takes approximately 5 minutes.

Continue stirring the emulsion, at the same speed, for 30-40 minutes. At the end of the process, the temperature of the emulsion will be 20-25° C.

The final stage is maturation of the emulsion. This stage is of variable duration, generally 48-72 hours, sufficient time for verifying its stability.

With emulsions prepared in this way, tests were carried out, as described below in the examples.

EXAMPLE 1

Antifibrotic Effect of P144 on Bleomycin-induced Fibrosis: Histopathological Evaluation Two emulsions or creams were prepared, an emulsion containing peptide P144 and a control emulsion with the vehicle for administration but without P144.

The control emulsion with the vehicle for administration was prepared by a procedure that starts with mixing of the components that are shown below in Table 2:

TABLE 2

Composition of the lipophilic phase of the emulsion

| Component | Amount (g) |
| --- | --- |
| Dimethicone 350 | 10 |
| Liquid paraffin | 40 |
| Chlorocresol | 0.1 |
| Cetrimide | 0.5 |
| Cetostearyl alcohol | 5 |

Next, this mixture was heated at 70° C. and was emulsified with 44.4 g of distilled water (also at 70° C.).

The emulsion containing the P144 was prepared as previously, except that the 44.4 g of water was replaced with a mixture of 44.28 g of water plus 0.010 g of P144 previously dissolved in 100 μl of dimethylsulphoxide.

The test was carried out using 6-week-old female C3H mice, supplied by Harlan SL (Spain). Development of skin sclerosis in the mice was induced by the administration of bleomycin (Sigma, Spain) dissolved in PBS at a concentration of 100 μg/ml and sterilized by filtration. The mice were injected with the bleomycin subcutaneously in the skin of the back, previously shaved, at daily doses of 100 μl of the solution in PBS injected with size 27 needles. The mice used as control received 100 μl of PBS without bleomycin. The injections were administered daily, at the same site, for 4 weeks.

The mice treated with bleomycin were divided into groups of 10 mice. In one group, 100 μl of the preparation of the emulsion containing P144 was applied daily in the shaved area of the skin, for the 4 weeks of bleomycin injections, whereas the other group received the control emulsion with the vehicle for administration. No composition was applied to the third group. The mice that were injected with PBS without bleomycin also did not receive any composition by topical administration.

The mice were sacrificed by asphyxiation by inhalation of $CO_2$, 24 hours after the last injection. The skin was removed from the back and biopsy specimens with diameter of 4 mm were obtained using a hole-making punch; these were frozen for subsequent protein analysis, whereas additional samples of skin were frozen in liquid nitrogen and were embedded in the medium known as "Tissue Tek® O.C.T. compound" (Optimal Cutting Temperature), supplied by SAKURA, the Netherlands, a medium for tissue protection by cryopreservation and then histological section, for subsequent histological and immunohistochemical investigations. The study was approved by the Ethical Committee of Complutense University of Madrid.

For the histological investigations, the skin sections were stained with haematoxylin and eosin (staining which makes the cell nuclei appear blue by reaction of the nucleic acids with the basic dye haematoxylin, whereas the cytoplasm is stained pink or red by reaction of the basic proteins present in it with the acidic dye eosin), Masson trichrome stain (which stains collagen fibres blue, the nuclei black and the background red) and toluidine blue for metachromatic staining of mast cells.

For the histomorphometric analyses, three fields of each skin biopsy were photographed at random and were digitized using a Spot RT CCD camera and Spot 4.0.4 software (Diagnostic Instruments, Sterling Heights, Mich.). This provided measurement of the thickness of the dermis, and from the digitized images it was possible to count the number of myofibroblasts (Example 2), fibroblasts positive for phosphorylated SMAD2/3 (Example 2) or mast cells (data not shown) corresponding to each field at 400× magnification.

The results obtained are shown in the first two rows of photographs in FIG. 1, whereas the last row corresponds to the processing of samples obtained in the test that will be described later in Example 3. It can be seen from these that the mice treated with bleomycin (BLEO) showed a marked increase in the collagen matrix of the dermis. In part A in the figure, corresponding to staining of the dermis with haematoxylin and eosin, it can be seen that there is an increase in thickness of the dermis in the mice treated with bleomycin which partially replaced the subcutaneous fat in comparison with the mice treated only with phosphate-buffered saline (PBS). Part B in the figure, corresponding to staining of the hypodermic area located on the panniculus carnosus muscle with Masson trichrome stain, shows that there was also an increase in the collagen matrix around the superficial fascia of the panniculus carnosus in the mice treated with bleomycin (BLEO). In these mice we also observed an abundant inflammatory infiltrate, composed principally of mononuclear cells as well as an increase in the number of mast cells, many of which showed signs of degranulation (data not shown).

The mice treated with peptide P144 (photographs labelled as a-TGF) during the weeks of the treatment with bleomycin showed a decrease in the area of dermal collagen (part A in FIG. 1) and hypodermic collagen (part B in FIG. 1) in comparison with the mice treated with the vehicle (VEHIC).

Figure 2:
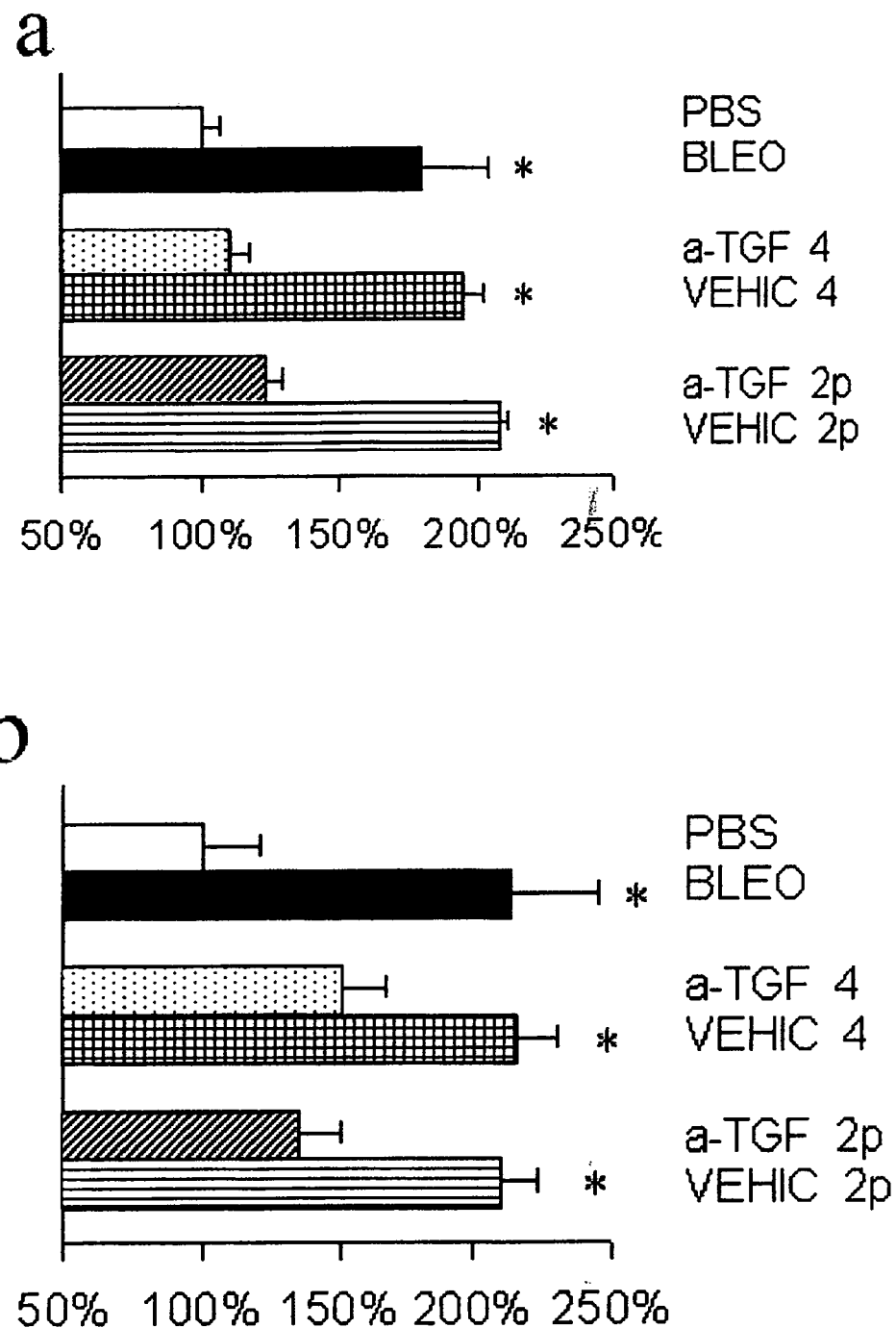
FIG. 2 shows graphs evaluating the effect of administration of an emulsion containing peptide P144 on the thickness of the dermis (graph in part A of the figure) and the content of soluble collagen (graph in part B of the figure), both calculated, for each treatment group, as mean±standard deviation of the percentage relative to the values found in the mice treated with phosphate buffered saline, adjusted to 100%. Each bar corresponds to the following treatments: unfilled bars (labelled "PBS"): mice injected with PBS for 4 weeks; bars with dark shading ■ (labelled "BLEO"): mice injected with bleomycin for 4 weeks, without any composition being applied topically; bars filled with dots (labelled "a-TGF 4"): mice injected with bleomycin for 4 weeks with simultaneous topical application of an emulsion containing peptide P144; bars filled with a network of horizontal and vertical lines ++ (labelled "VEHIC 4"): mice that were injected with bleomycin for 4 weeks with simultaneous topical application of an emulsion that only contained the vehicle for administration; bars filled with inclined lines (//) (labelled "a-TGF 2p"): mice that received injections of bleomycin for 4 weeks and to which an emulsion containing peptide P144 was administered topically for the next 2 weeks; bars filled with horizontal lines (=) (labelled "VEHIC 2p"): mice that received injections of bleomycin for 4 weeks and to which an emulsion containing only the vehicle for administration was administered topically for the next 2 weeks. *: $p<0.05$.

The thickness of the dermis was measured on the digitized images of the sections stained with haematoxylin and eosin, and then the percentage variation in thickness of the dermis was calculated relative to the mean of the values obtained for the mice treated with PBS, adjusted to 100%. The data obtained are shown in the graph in part A of FIG. 2, where each bar represents the value of the mean±standard deviation of 10 mice per group. It can be seen in this graph that the thickness of the dermis decreased significantly in the mice treated with P144 (bar filled with dots) relative to the mice treated with the vehicle (bar filled with a network of horizontal and vertical lines), which displayed a thickness similar to that found in the mice treated with bleomycin which did not receive topical treatment (bar with dark shading). The other two bars of the graph correspond to samples obtained in the test described later in Example 3.

To confirm the histological observation of decrease in fibrosis in mice treated with P144, the content of pepsin-soluble collagen was determined in 4-mm biopsies obtained with a punch. The pepsin-soluble collagen is an extractable fraction that represents the collagen recently synthesized in the tissues. To quantify it, after homogenizing the biopsies, the pepsin-soluble collagen was extracted over night using 5 mg/ml of pepsin in 0.5 mol/l of acetic acid. The content of soluble collagen was determined using the kit for calorimetric testing of collagen based on Sircol™ (Biocolor, Northern Ireland), following the manufacturer's instructions, obtaining the results shown in the graph in part B of FIG. 2, where each bar once again represents the mean±standard deviation of 10 mice per group corresponding to the percentage variation of the content of soluble collagen in each sample calculated relative to the content of soluble collagen measured in the samples treated with PBS, for which the values were adjusted to 100%. This analysis showed a significant decrease in the content of soluble collagen in the mice treated with P144 (bar filled with dots).

No changes were observed in the density of infiltration of inflammatory cells or of infiltration of mast cells, nor morphological changes in the epidermis of the mice treated with the vehicle or with P144 when compared with the mice that only received injections of bleomycin (data not shown).

EXAMPLE 2

Characterization of the Cellular Effects of P144: Immunohistochemical Tests

Figure 3:
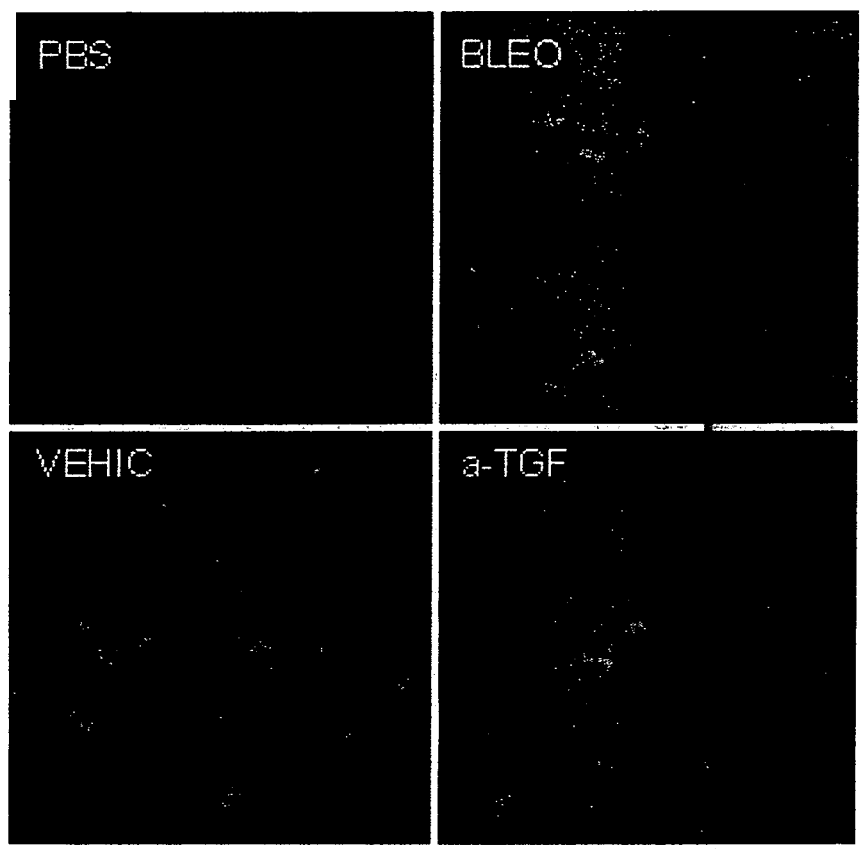
FIG. 3 corresponds to the immunofluorescent detection of myofibroblasts in skin sections from mice used in tests for evaluating the effect of topical application of P144 on bleomycin-induced skin sclerosis. The photographs in part A correspond to sections labelled with an anti-smooth muscle α-actin (SMA) antibody bound to fluorescein isothiocyanate (FITC) and examined with a fluorescence microscope. |Part B of the figure shows a graph of the mean value±standard deviation of the number of SMA-positive cells present per field in each of the samples. Samples: PBS: mice injected with PBS for 4 weeks; BLEO: mice injected with bleomycin for 4 weeks, without any composition being applied topically.
Figure 3:
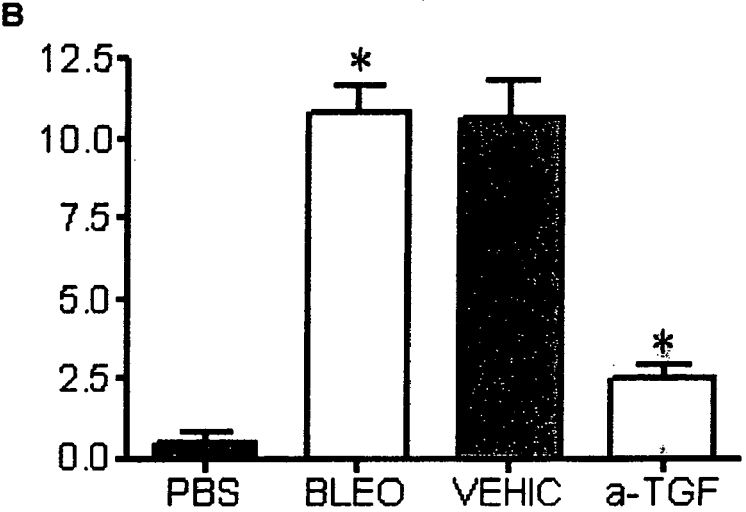

For more extensive characterization of the cellular effects of neutralization of TGF-β1 with P144, various immunohistochemical studies were carried out, analysing the effect of the peptide on the development of myofibroblasts positive for α-SMA and the induction of SMAD2/3 in fibroblasts induced by bleomycin. For this, immunofluorescent staining was carried out (with an anti-smooth muscle α-actin (SMA) monoclonal antibody labelled with fluorescein isothiocyanate (FITC), supplied by Sigma) of skin sections obtained in the test described previously in Example 1, and the samples obtained were examined with an Axioplan-2 fluorescence microscope from Zeiss (Germany). FIG. 3 shows photographs obtained from samples corresponding to mice that were only injected with PBS (PBS), mice that had received injections of bleomycin for 4 weeks (BLEO), mice after topical administration of an emulsion that only contained the vehicle for administration during the weeks of treatment with bleomycin (VEHIC) or mice that were administered an emulsion that contained in addition the P144 peptide (a-TGF). The graph in the bottom part B of said FIG. 3 shows a graph showing the results of evaluation of the number of cells that are positive for the presence of α-SMA quantifiable per field, calculated from the fluorescence signal obtained; each bar represents the mean standard deviation of the data corresponding to 10 mice per group.

The results show that in the control mice, myofibroblasts that are positive for α-SMA were observed very rarely, whereas an abundant number of these cells was observed after four weeks of injections of bleomycin. The mice treated with P144 showed a significant reduction in the number of myofibroblasts positive for α-SMA in comparison with the mice treated only with the vehicle.

In addition, we also carried out immunohistochemical detection of phosphorylated SMAD2/3 in skin sections. For this, the samples were labelled with a specific anti-phospho-SMAD2/3 polyclonal antibody, supplied by Santa Cruz Biotechnology (Santa Cruz, Calif.) and a method based on biotin peroxidase (ABC, Vector Laboratories, Burlingame, Calif.). The slides were developed using a diaminobenzidine (DAB) chromogen. The sections were contrast-stained with Gill's haematoxylin. The results are shown in FIG. 4, where in part A (corresponding to the photographs obtained from mice submitted to each of the treatments described) the fibroblasts labelled with the antibody are arrowed. Part B of FIG. 4 shows a graph in which each bar corresponds to the mean value±standard deviation of the number of fibroblasts positive for presence of phospho-SMAD2/3 detectable per observation field. In this case, the data are only representative of five mice per treatment group.

The data obtained in this second immunostaining indicate an increase in the number of dermal fibroblasts displaying phosphorylation of SMAD2/3 in the mice that were injected with bleomycin, which confirms earlier observations in this animal model (Takagawa et al., 2003). The number of fibroblasts positive for phospho-SMAD2/3 decreased significantly in the mice treated with P144 in comparison with the mice treated with the vehicle.

Finally, we undertook determination of whether there is any effect on regulation of CTGF expression induced by peptide P144 in the mice treated with bleomycin. For this, immunohistochemical tests were carried out with the L-20 polyclonal antibody (Santa Cruz Biotechnology, Santa Cruz, Calif.), a specific anti-CTGF antibody which was used for staining skin sections from mice corresponding to each of the treatment groups described in Example 1, with the presence of the antibody bound to the samples being revealed by means of a DAB substrate and then performing contrast staining with Gill's haematoxylin. In the test described in Example 2, this L-20 antibody specifically recognized a unique protein of 38 kD, which was induced strongly by treatment with TGF-β1 in cultured fibroblasts (data not shown). With respect to the samples obtained from the mice, the data shown in FIG. 5 demonstrate that CTGF expression was induced strongly in the fibroblasts as well as in the cells of the epidermis and of the epithelial hair follicle of the mice treated with bleomycin. Treatment with P144 caused a clear decrease in CTGF expression in the epidermis and the hair follicles, in comparison with mice treated with the vehicle only, whereas CTGF was still detectable in fibroblasts after treatment with P144.

EXAMPLE 3

Antifibrotic Effect of P144 on Fibrosis Established by Injections of Bleomycin

To evaluate the effect of treatment of mice which already had an established fibrosis, a test was carried out similar to that described in Example 1, except that the mice did not receive any composition by the topical route in the four weeks during which they were administered injections of bleomycin. At the end of the four weeks, a topical composition was applied to the mice daily for two weeks before they were sacrificed: the emulsion containing P144 was administered to one group of mice, whereas the emulsion that only contained the vehicle for administration was administered to the other group. After the mice were sacrificed, skin samples were taken from the back in a manner similar to that described in the test in Example 1 and they were examined histologically and pepsin-soluble collagen was quantified following the procedures described previously in Example 1.

Figure 1:
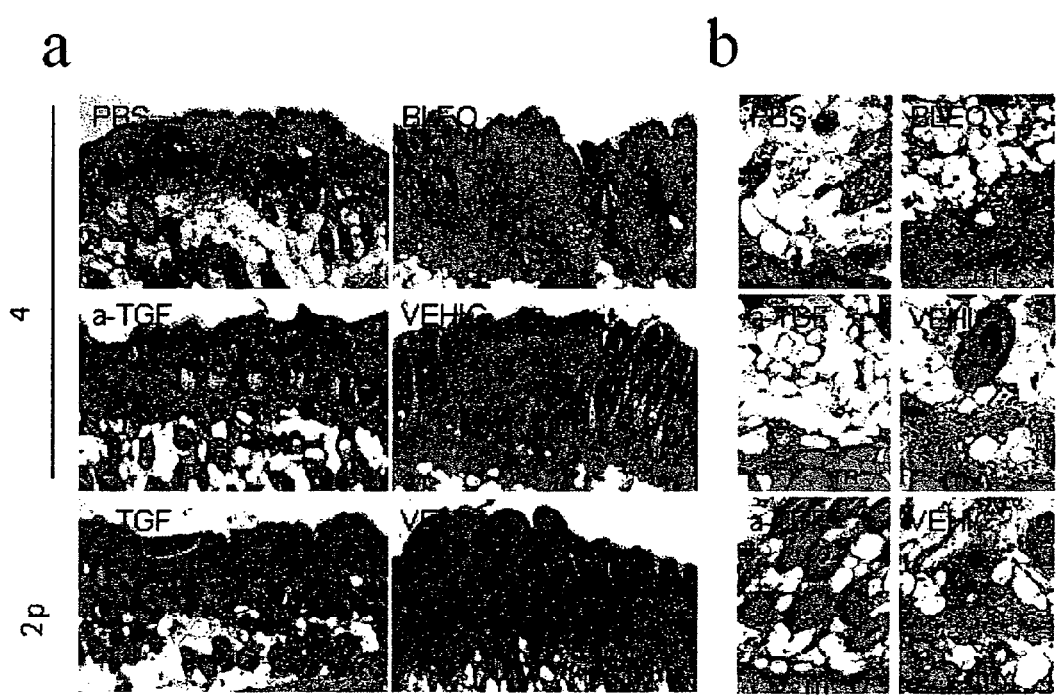
FIG. 1 shows photographs of stained skin sections from mice used in tests for histopathological evaluation of the effect of topical application of P144 on bleomycin-induced skin sclerosis. The photographs in the top and middle rows (headed with the number "4") correspond to tests of injection of bleomycin for 4 weeks and simultaneous topical application of an emulsion containing peptide P144 (photographs labelled a-TGF) or of an emulsion containing only the vehicle for administration (photographs labelled "VEHIC"), with the samples labelled "BLEO" corresponding to mice that were injected with bleomycin without applying any composition topically, whereas the samples labelled "PBS" correspond to mice that only received phosphate buffered saline in the injections, and also did not receive any composition by the topical route. The photographs in the bottom row (headed "2p") correspond to samples obtained in tests in which the mice received bleomycin injections for 4 weeks and that were administered topically, during the next 2 weeks, an emulsion that contained peptide P144 (photographs labelled "a-TGF") or alternatively an emulsion that only contained the vehicle for administration (photographs labelled "VEHIC"). The photographs in part A of the figure correspond to staining of the dermis with haematoxylin-eosin, whereas the photographs in part B of the figure correspond to the subcutaneous area located above the panniculus carnosus muscle (m) stained with Masson trichrome stain.

The photographs shown in the bottom row of FIG. 1 correspond to the data obtained in histopathological evaluation of bleomycin-induced skin sclerosis in these mice; part A shows the results of staining of the dermis with haematoxylin and eosin, whereas part B corresponds to staining of the hypodermic region located on the panniculus carnosus muscle (m) effected with Masson trichrome stain. Evaluations of the dermis thickness changes and the skin collagen content are shown, respectively, in the graphs in parts A and B of FIG. 2.

The data obtained show that the fibrosis persisted in the mice treated with the composition that only contained the vehicle (labelled VEHIC in the bottom part of FIG. 1 and represented by bars filled with inclined lines in the graphs in FIG. 2), whereas the mice treated with P144 for 2 weeks (labelled a-TGF in the bottom part of FIG. 1 and represented by the bars filled with horizontal lines in the graphs in FIG. 2) showed a significant decrease in thickness of the dermis and collagen content.

EXAMPLE 4

Antifibrotic Effect of P144 on Fibrosis Induced by High Doses of Bleomycin

An experiment was carried out similar to that described in Example 1, but using higher doses of bleomycin. For this, two emulsions were again prepared, one containing peptide P144 and a control emulsion with the vehicle for administration but without P144, using the same components and following the procedure described in Example 1.

Once again, the test was carried out using 6-week-old female C3H mice, with body weight of 15-18 g, supplied by Harlan S. L. (Spain). Development of skin sclerosis in the mice was induced by the administration of bleomycin (Sigma, Spain) dissolved in PBS and sterilized by filtration, but in this case the concentration of bleomycin in the solution was higher than in Example 1, 1 mg/ml. The mice were injected with the bleomycin subcutaneously in the shaved skin of the back, using size 27 needles, at a dose of 100 μl of bleomycin in PBS, so that the dose of bleomycin injected in each mouse was approximately 6 mg/kg body weight. The injections were administered at the same site, on alternate days, for 4 weeks. The mice used as control received 100 μl of PBS without bleomycin.

In all, 15 mice were used for the experiment, and were divided into 3 treatment groups, each comprising 5 mice. The treatments received by each of the groups were:

Group PBS: 100 μl of PBS without bleomycin every 48 hours

Group BLEO+Vehic: 100 μl of PBS with bleomycin (1 mg/ml) on alternate days for 4 weeks+100 μl of emulsion without P144 daily for the same 4 weeks.

Group BLEO+P144: 100 μl of PBS with bleomycin (1 mg/ml) on alternate days for 4 weeks+100 μl of emulsion with P144 (0.1 mg/ml) daily for the same 4 weeks.

The mice were sacrificed by asphyxiation by inhalation of $CO_2$, 24 hours after the final injection or after the last topical administration of emulsion. The skin was removed from the back and biopsy specimens with a diameter of 4 mm were obtained using a punch, and were frozen for subsequent protein analysis, whereas additional skin samples were processed for later histological and immunohistochemical investigations as in Example 1.

For the histological investigations, the skin sections were stained with haematoxylin and eosin. The histomorphometric analyses were also carried out as in Example 1, by randomly photographing three fields of each skin biopsy and digitizing them using a Spot RT CCD camera and Spot 4.0.4 software (Diagnostic Instruments, Sterling Heights, Mich.), obtaining digitized images on which the thickness of the dermis was measured.

The results are shown in FIG. 6 (which shows an image representative of each of the five mice forming the different groups) and in FIG. 7 (showing the percentage variation in thickness of the dermis relative to the mean of the values obtained in mice treated with PBS, adjusted to 100%). An increase in thickness of the dermis in the mice treated with bleomycin can be seen, which almost completely replaced the subcutaneous fat in the mice treated additionally with the emulsion that only contained the vehicle for administration (samples labelled "BLEO+Vehic"); they were also observed to have an increase in the collagen matrix around the superficial fascia when compared with the mice treated only with PBS (samples labelled "PBS"). The mice treated with bleomycin and peptide P144 (samples labelled "BLEO+P144") displayed a significant decrease in area of dermal and hypodermic collagen relative to the mice treated with bleomycin and the emulsion that only contained the vehicle for administration.

Galenical Development

Once the effect of topical application of P144 on distinctive features of fibrosis had been demonstrated, changes were made to the formulation used for obtaining the compositions in the form of lipogel used in the previous examples, with the aim of finding formulations that are more suitable for topical application of P144 in humans. The original formulation gave rise to extremely greasy compositions, which could cause stains on clothing, and moreover had high viscosity, making it difficult to spread them on the skin, giving low fluidity at room temperature, which was a drawback for their large-scale production and their dosing in commercial presentation forms. Therefore separate tests were carried out in which the composition of the original formulation was varied with the aim of finding a pharmaceutical form of lower viscosity than the original, which will flow and allow processing in machines for semisolid forms, with pleasant appearance, good spreadability and preserving their characteristics of local action. The majority of the tests described were intended to eliminate or reduce the content of cetostearyl alcohol, which is responsible for the high viscosity. The products previously mentioned in Table 1 and the method of preparation described after Table 2 were used for preparing the various compositions.

EXAMPLE 5

Galenical Development: Reduction of the Content of Cetostearyl Alcohol

Firstly, the content of cetostearyl alcohol, which is responsible for the high viscosity, was reduced by increasing the percentage of water in the formulation. The other components in the formulation were maintained in their initial proportions. Thus, the formulations shown in Table 3 were tested; all the percentages correspond to weight/weight ratios (w/w).

TABLE 3

Formulations with partial replacement of cetostearyl alcohol with water.

| Component | Formulation 1 | Formulation 2 | Formulation 3 | Reference formulation |
|---|---|---|---|---|
| Dimethicone 350 | 10% | 10% | 10% | 10% |
| Liquid paraffin | 40% | 40% | 40% | 40% |
| Chlorocresol | 0.1% | 0.1% | 0.1% | 0.1% |
| Cetrimide | 0.5% | 0.5% | 0.5% | 0.5% |
| Cetostearyl alcohol | 1% | 2% | 3% | 4% |
| Purified water q.s.f. | 100% | 100% | 100% | 100% |

As was hoped, the viscosity of the semisolid preparation decreases when the percentage of cetostearyl alcohol decreases. After 24 hours at room temperature, all the formulations remained stable. The formulation with higher content of cetostearyl alcohol (No. 4) was still excessively viscous, extremely greasy and of very low fluidity. In contrast, formulations 2 and 3 were less viscous and had pleasant organoleptic characteristics; however, their fluidity was still inadequate. Finally, formulation 1 had good organoleptic characteristics, reduced viscosity and good fluidity.

400 g of each of these formulations was prepared for investigating their behaviour in the dosing machine, and it was found that formulations 1 and 2 flowed adequately. However, the other formulations were excessively viscous.

EXAMPLE 6

Galenical Development: Partial Replacement of Cetostearyl Alcohol with Liquid Paraffin In this case a proportion of the cetostearyl alcohol was replaced with liquid paraffin with the aim of obtaining a formulation that flows adequately and remains stable. Another five different emulsions were prepared, combining different percentages of cetostearyl alcohol and liquid paraffin, which were selected taking into account the specific characteristics of each of them and their contribution to the fluidity and stability of the final emulsion. These emulsions were designated: 1', 2', 3', 4' and 5'. Their composition is summarized in Table 4, where, unless stated otherwise, percentages correspond to weight/weight ratios (w/w).

TABLE 4

Composition of formulations 1', 2', 3', 4' and 5'.

| Component | F. 1' | F. 2' | F. 3' | F. 4' | F. 5' | Reference formulation |
|---|---|---|---|---|---|---|
| Dimethicone 350 | 10% | 10% | 10% | 10% | 10% | 10% |
| Liquid paraffin | 44% | 43.5% | 43% | 42.5% | 42% | 40% |
| Chlorocresol | 0.1% | 0.1% | 0.1% | 0.1% | 0.1% | 0.1% |
| Cetrimide | 0.5% | 0.5% | 0.5% | 0.5% | 0.5% | 0.5% |
| Cetostearyl alcohol | 1% | 1.5% | 2% | 2.5% | 3% | 4% |
| Purified water q.s.f. | 100% | 100% | 100% | 100% | 100% | 100% |

Formulation 1' was very fluid and of low viscosity. Formulation 2' had the same characteristics as 1', but generated persistent foam during manufacture. 3' had some characteristics similar to 2', except for its higher viscosity and therefore lower fluidity than 2'. As for Formulations 4' and 5', they were found to be very viscous, and with fluidity similar to the starting formulation.

Next, small batches of emulsions 1' to 5'(500 ml) were manufactured, and were used for more extensive dosing tests. Formulations 1', 2' and 3' were the most suitable, displaying suitable fluidity for homogeneous dosing in the manufacture of large batches.

EXAMPLE 7 (COMPARATIVE)

Galenical Development: Complete Replacement or Elimination of the Cetostearyl Alcohol With the aim of improving the viscosity characteristics of the formulation on the one hand and simplifying production of the cream on the other hand (by eliminating or reducing preheating to permit mixing of the components in the presence of cetostearyl alcohol), the complete replacement of the latter or its elimination was investigated.

6.1. Complete Replacement of the Cetostearyl Alcohol with Hydrophilic Emulsifiers.

Two formulations were prepared, replacing the cetostearyl alcohol with two hydrophilic emulsifiers that were incorporated in the aqueous phase: Tween 80 (4%) or sodium laurylsulphate (1%). This gave rise to the formulations shown in Table 5, in which, unless stated otherwise, the percentages correspond to weight/weight ratios (w/w).

TABLE 5

Formulations A and B with hydrophilic emulsifiers.

| Component | Formulation A Percentage | Formulation B Percentage |
|---|---|---|
| Dimethicone 350 | 10 | 10 |
| Liquid paraffin | 40 | 40 |
| Chlorocresol | 0.1 | 0.1 |
| Cetrimide | 0.5 | 0.5 |
| Tween 80 | 4 | — |
| Sodium laurylsulphate | — | 1 |
| Purified water q.s.f. | 100 | 100 |

After a short period of rest at room temperature (24 hours) the emulsions broke in both formulations, and so were discarded.

6.2. Complete Replacement of the Cetostearyl Alcohol with Liquid Paraffin.

Once again an attempt was made to eliminate the cetostearyl alcohol from the formulation, this time by increasing the percentage of liquid paraffin (Formulation C, shown in Table 6) and by adding stringy vaseline (Formulation D, shown in Table 7). In both formulations, unless stated otherwise, the percentages correspond to weight/weight ratios (w/w).

TABLE 6

Formulation C.

| Component | Percentage |
|---|---|
| Dimethicone 350 | 10 |
| Liquid paraffin | 43 |
| Chlorocresol | 0.1 |
| Cetrimide | 0.5 |
| Purified water q.s.f. | 100 |

TABLE 7

Formulation D.

| Component | Percentage |
|---|---|
| Dimethicone 350 | 10 |
| Liquid paraffin | 43 |
| Chlorocresol | 0.1 |
| Cetrimide | 0.5 |
| Stringy vaseline | 5 |
| Purified water q.s.f. | 100 |

The result obtained with Formulation C was that, after a period of maturation at room temperature (less than 24 hours), the emulsion broke, and so was discarded. Although initially the emulsion of Formulation D remained stable and very liquid, after two days at rest at room temperature it began to release water, a sign of poor stability of the emulsion, and therefore it too was discarded.

6.3. Replacement of the Cetostearyl Alcohol with Aristoflex AVC®.

A new formulation was tested starting from the aforesaid Formulation 1, in which half of the cetostearyl alcohol was replaced with Aristoflex AVC®. This is an excipient indicated for the formulation of hydrophobic gels, and endows them with great fluidity.

TABLE 8

Composition of the formulation with Aristoflex AVC ®.

| Component | Percentage (w/w) |
|---|---|
| Dimethicone 350 | 10 |
| Liquid paraffin | 40 |
| Chlorocresol | 0.1 |
| Cetrimide | 0.5 |
| Cetostearyl alcohol | 0.5 |
| Aristoflex AVC | 0.5 |
| Deionized water q.s.f. | 100 |

In a few hours at rest, this emulsion broke, therefore it too was discarded.

6.4. Complete Removal of the Cetostearyl Alcohol.

To eliminate the need to apply heat in the production process, a new formulation was tested without cetostearyl alcohol, as this is the only component in the formulation that needs to be heated, to melt it and enable it to be mixed with the rest of the formulation.

This new modification means that tests have to be carried out for dissolving the chlorocresol in water. After various tests, it was verified that this product cannot be dissolved in water. After a brief review of the literature, ethanol was tested as cosolvent in the aqueous phase for dissolving the chlorocresol.

TABLE 9

Composition of the formulation without cetostearyl alcohol.

| Component | Percentage (w/w) |
|---|---|
| Dimethicone 350 | 10 |
| Liquid paraffin | 40 |
| Chlorocresol | 0.1 |
| Cetrimide | 0.5 |
| Ethanol | 1 |
| Purified water q.s.f. | 100 |

Once the emulsion was prepared, after a short period of maturation at room temperature the emulsion broke. This is due to the complete absence of cetostearyl alcohol.

EXAMPLE 8

Galenical Development: Replacement of the Chlorocresol and Inclusion of P144

Finally, we decided to make small changes to formulation 2', selected as one of the most suitable on the basis of its characteristics of easy dosing and cutaneous adsorption, with the aim of replacing the chlorocresol with antimicrobials that are more suitable for topical formulations. In addition, peptide P144, and DMSO as solvent thereof, were added. These changes did not affect the behaviour of the emulsion. The definitive composition of the formulation that was considered to be the most suitable for the manufacture of a medicinal product intended for the treatment of skin fibrosis by topical administration is that shown in Table 10, in which, unless stated otherwise, the percentages correspond to weight/weight ratios (w/w).

TABLE 10

Suitable composition of the emulsion for the administration of P144.

| Component | Percentage |
|---|---|
| Dimethicone 350 | 10% |
| Liquid paraffin | 43.5% |
| Cetrimide | 0.5% |
| Methylparaben | 0.02% |
| Propylparaben | 0.01% |
| Cetostearyl alcohol | 1.5% |
| DMSO | 0.1%* |
| P144 | 0.01% |
| Purified water q.s.f. | 100% |

*Weight/volume ratio (w/v)

EXAMPLE 9

Percutaneous Absorption of P144

In order to assess the cutaneous penetration of peptide 144, and of P144 in a semisolid preparation (P144 emulsion), a preliminary study of percutaneous absorption was carried out. For this purpose in vitro penetration tests using dermatomized pig ear skin were conducted (Santoyo et al., 2002a and 2002b). Porcine skin, specifically the outer region of the ear, was chosen since its use for permeation experiments has been extensively documented (Bhatia and Singh, 1998) and it is well suited for representing the human skin permeability (Simon and Maibach, 2000).

The substance of reference for the study was P144, supplied by NeoMPS SA (Strasbourg, France; Batch number HF 320440; Storage conditions: −20° C.).

The test product was the semisolid preparation containing P144 (P144 emulsion; P144 concentration was 0.01% w/w). A single dose of 100 µg/ml of P144 emulsion was tested, with sampling in the diffuser compartment at 4 different timepoints (0, 2, 6, 12 and 24 hours).

Two additional control preparations were used for the experiments,

Control A: Solution of P144 in 1 ml acetic acid (100% glacial acetic acid Merck, Batch number: K 34022763 447) diluted to the same concentration used for the test product; and Control B: Emulsion without P144 (Wehic).

Composition of test product and control preparations is shown on Table 11, where, unless stated otherwise, all the percentages correspond to weight/weight ratios (w/w).

TABLE 11

Compositions of the test product, control vehicle, and control peptide P144 solution.

| | Test product P144 emulsion | Control B Vehic | Control A P144 Solution |
|---|---|---|---|
| Dimethicone 350 | 10.0% | 10.0% | — |
| Paraffin | 43.5% | 43.5% | — |
| Methylparaben | 0.02% | 0.02% | — |
| Propylparaben | 0.01% | 0.01% | — |
| Cetrimide | 0.5% | 0.5% | — |
| Cetostearylic alcohol | 1.5% | 1.5% | — |
| DMSO | 0.2%* | 0.2%* | — |
| Peptide P144 | 0.01% | — | 0.01% |
| Purified water | q.s.f. 100.0% | q.s.f. 100.0% | |
| Glacial acetic acid | | | q.s.f. 100.0% |

Purified water (type II) was obtained with a Wasserlab system (Automatic Model no. AU 050503).
*Weight/volume ratio (w/v); q.s.f.: quantity sufficient for The pig ear skin was obtained from hybrid pigs destined for human consumption.

The permeation test was performed in a Franz diffusion cell system Franz 57-100-828 (Hanson Research). The Franz cell apparatus consists of 12 borosilicate and Teflon glass cells divided into two blocks (A and B, with 6 cells each). Each cell in turn is composed of a receptor compartment (volume 4.5 ml) and a donor compartment (diffusion surface 0.636 cm$^2$).

The test product or its control is placed on the donor compartment, while in the receptor compartment we place the solution to collect the amount of drug crossing the experimental system (pig skin in this case). This experimental system is located at the interface between the donor and receptor compartments.

In the donor compartment, in cells 1, 2 and 3 of side A, 1 ml was added of P144 solution (Control A; concentration of 100 µg/ml). In cells 4, 5 and 6 of side A, and in cells 1, 2 and 3 of side B, we added 1 ml of P144 emulsion (test product; P144 concentration of 100 µg/ml). Finally, in cells 4, 5 and 6 of side B we added 1 ml of the vehicle (Control B) without peptide.

In the first place a dermatomization step was conducted. The porcine ears are washed, manipulated and sectioned into adequate portions using a dermatome (Aesculap-Wagner dermatome C. GA 630; B. Braun Surgical S.A., Barcelona, Spain) to obtain a membrane with a thickness of 1 mm. The portions of skin are stored separately at −20° C., using Tissue Tek® OCT Compound (Sakura, ref.: 4583) as a cryoprotectant.

Secondly, the percutaneous diffusion test was conducted as follows. A 24-hour diffusion study is made, testing the P144 emulsion containing 100 µg of peptide P144/ml. This concentration has been defined as one of the suitable concentrations for use in humans. As diffusion membrane, use is made of pig ear skin dermatomized to 1.0 mm.

Prior to testing, the skin specimens are hydrated by immersion for 30 minutes in isotonic phosphate buffer solution (PBS)(Sigma, ref. P4417-100 TAB; pH 7.2-7.3). On the other hand, the receptor of each of the cells is filled with 4.5 ml of PBS adjusted to pH 7.4±0.2. On this receptor compartment we place the dermatomized and hydrated portion of skin and, over the experimental system, we position the donor compartment (with a diffusion surface of 0.636 cm$^2$). In the donor compartment we place 1 ml of the test product or control preparations.

The receptor is maintained at a temperature of 37.0±0.5° C. and under stirring conditions (300 rpm). At predetermined time intervals (0 h, 2 h, 6 h, 12 h and 24 h) 1 ml samples are collected from the receptor compartment, this volume then being replaced by 1 ml of original solution to maintain the receptor volume constant.

The collected samples are stored in identified cryotubes at −80° C. for posterior chromatographic analysis.

Finally, for completing the study a quantification of peptide P144 in the collected samples was carried out using high performance liquid chromatography with mass spectrometry (HPLC/MS).

Prior to injection of the different samples into the liquid chromatograph, they were centrifuged (Abbott table centrifuge) at 10,800 rpm during 5 minutes.

The following chromatographic conditions were used:
Equipment: Liquid chromatograph Hewlett-Packard 1100
Column: Zorbax SB $C_{18}$ 3.5 µm 150×4.6 mm (Agilent)
Precolumn: Zorbax 300 SB-$C_{18}$ 5 µm 12.5×4.6 mm (Agilent)
Detection: MS/MS
 Ionization: electrospray, positive
 Ions (m/z): 1580.09→791.1;
 Detector parameters:
 Temperature 350° C.
 Carrier gas flow rate 10 l/min
 Nebulizer pressure 50 psig
 Capillary voltage 4500 V
Mobile phase: acetonitrile: elution buffer (38:62) at a flow rate of 0.5 ml/min (elution solution: aqueous solution of trifluoroacetic acid (TFA), at a concentration of 0.05% (w/v)
Temperature of the column: 25±3° C.
Injection volume: 10 µl
Duration of chromatogram run: 6 min.

FIG. 8 shows a chromatogram corresponding to the analysis of a sample of an aqueous solution with 0.1% TFA at a concentration of 100 ng/ml. The retention time obtained for the peak of interest (P144) is approximately 4.5 minutes. Under the chromatographic conditions described in Material and Methods, it is possible to quantify the peptide in aqueous solutions over a concentrations range of between 0.1 and 1000 ng/ml of sample (r>0.996).

FIG. 9 shows the mass spectrum of the peptide, obtained after analysis of a sample with a concentration of 1000 ng/ml.

FIG. 10 shows the cutaneous permeability profile of P144 from the semisolid formulation (Test product). In all cases, the amount of peptide P144 capable of crossing the pig skin membrane was below the detection limit of the analytical technique used. Therefore, in all cases the concentration of P144 in the sample analyzed is undetectable and inferior to 30 pg/ml—the latter being the limit of detection (LOD) established for the analytical method employed.

Likewise, P144 solution (Control A) did not facilitate arrival of the drug in the receptor compartment. In this case, in the same way as from P144 emulsion, the amount of peptide P144 capable of crossing the biological membrane was below the detection limit of the analytical technique used.

Under the experimental conditions of the present study, it can be concluded that peptide P144 is not capable of crossing the pig skin membrane when administered in the semisolid P144 emulsion presenting the composition indicated in Table 11.

REFERENCES

Akhurst R J: TGF-beta antagonists: Why supress a tumor supressor? J Clin Invest 109:1533-1536, 2002

Bhatia, K. S. and Singh, J. Mechanism of transport enhancement of LHRH through porcine epidermis by terpenes and iontophoresis: permeability and lipid extraction studies. Pharm. Res. 15:1857-1862, 1998

Bottinger E P, Letterio J J, Roberts A B: Biology of TGF-beta in knockout and transgenic mouse models. Kidney Int 51:1355-1360, 1997

Brahmatewari J, Serafini A, Serralta V, Mertz P M, Eaglstein W H: The effects of topical transforming growth factor-beta2 and anti-transforming growth factor-beta2,3 on scarring in pigs. J Cutan Med Surg 4:126-131, 2000

Daniels C E, Wilkes M C, Edens M, Kottom T J, Murphy S J, Limper A H, Leof E B: Imatinib mesylate inhibits the profibrogenic activity of TGF-beta and prevents bleomycin-mediated lung fibrosis. J Clin Invest 114:1308-1316, 2004

Everett E T, Pablos J L, Harley M, LeRoy E C, Norris J S: The role of mast cells in the development of skin fibrosis in tight-skin mutant mice. Comp Biochem Physiol A Physiol 110:159-165, 1995

Frazier K, Williams S, Kothapalli D, Klapper H, Grotendorst G R: Stimulation of fibroblast cell growth matrix production, and granulation tissue formation by connective tissue growth factor. J Invest Dermatol 107:404-411, 1996

Hopp T. P. and Woods, K. R.: Prediction of protein antigenic determinants from amino acid sequences. Proc. Natl. Acad. Sci. USA 78, No. 6: 3824-3828, 1981.

Igarashi A, Nashiro K, Kikuchi K, et al: Connective tissue growth factor gene expression in tissue sections from localized scleroderma, keloid, and other fibrotic skin disorders. J Invest Dermatol 106:729-73.1, 1996

Jelaska A, Korn J H: Role of apoptosis and transforming growth factor beta1 in fibroblast selection and activation in systemic sclerosis. Arthritis Rheum 43:2230-2239, 2000.

Jester J V Barry-Lane P A, Petroll W M, Olsen D R, Cavanagh H D: Inhibition of corneal fibrosis by topical application of blocking antibodies to TGF beta in the rabbit. Cornea 16:177-187, 1997

Jimenez S A, Hitraya E, Varga J: Pathogenesis of scleroderma. Collagen. Rheum Dis Clin North Am 22:647-674, 1996

Lakos G, Takagawa S, Chen S J, et al: Targeted disruption of TGF-beta/Smad3 signaling modulates skin fibrosis in a mouse model of scleroderma. Am J Pathol 165:203-217, 2004

Leask A, Denton C P, Abraham D J: Insights into the molecular mechanism of chronic fibrosis: The role of connective tissue growth factor in scleroderma. J Invest Dermatol 122:1-6, 2004

McCormick L L, Zhang Y, Tootell E, Gilliam A C: Anti-TGF-beta treatment prevents skin and lung fibrosis in murine sclerodermatous graft-versus-host disease: A model for human scleroderma. J Immunol 163:5693-5699, 1999

Quan T, He T, Kang S, Voorhees J J, Fisher G J: Connective tissue growth factor: Expression in human skin in vivo and inhibition by ultraviolet irradiation. J Invest Dermatol 118: 402-408, 2002

Querfeld C, Eckes B, Huerkamp C, Krieg T, Sollberg s: Expression of TGF-beta 1, -beta 2 and -beta 3 in localized and systemic scleroderma. J Dermatol Sci 21:13-22, 1999.

Schiller M, Javelaud D, Mauviel A: TGF-beta-induced SMAD signaling and gene regulation: Consequences for extracellular matrix remodeling and wound healing. J Dermatol Sci 35:83-92, 2004

Santoyo S, Garcia de Jalon E, Ygartua P, Renedo M J, Blanco-Prieto M J. Optimization of topical cidofovir penetration using microparticles. Int. J. Pharm. 242:107-113, 2002a Santoyo S, Garcia de Jalon E, Campanero M A, Ygartua P. Determination of cidofovir in both skin layers and percutaneous penetration samples by HPLC. J. Pharm. Biomed. Anal. 29:819-826, 2002b Shi Y, Massague J: Mechanisms of TGF-beta signaling from cell membrane to the nucleus. Cell 113:685-700, 2003

Simon G A and Maibach H I. The pig as an experimental animal model of percutaneous qualitative and quantitative observations—an overview. Skin Pharmacol. Appl. Skin Physiol. 13:229-234, 2000

Yamamoto T, Takagawa S, Katayama I, Nishioka K: Anti-sclerotic effect of transforming growth factor-beta antibody in a mouse model of bleomycin-induced scleroderma. Clin Immunol 92:6-13, 1999b Yamamoto T, Takagawa S, Katayama I, Yamazaki K, Hamazaki Y, Shinkai H, Nishioka K: Animal model of sclerotic skin. I: Local injections of bleomycin induce sclerotic skin mimicking scleroderma. J Invest Dermatol 112:456-462, 1999c Yamamoto T, Takagawa S, Nishioka K: Mast cell-independent increase of type collagen expression in experimental scleroderma induced by bleomycin. Arch Dermatol Res 293: 532-536, 2001

Zhang Y, McCormick L L, Gilliam A C: Latency-associated peptide prevents skin fibrosis in murine sclerodermatous graft-versus-host disease, a model for human scleroderma. J Invest Dermatol 121:713-719, 2003

What is claimed is:

1. A method for preventing or treating a fibrotic disease or complications thereof on the skin of a subject comprising topically applying to the skin of the subject a composition comprising
   (a) a peptide that inhibits TGFβ1, said peptide being selected from the group consisting of:
      i) SEQ ID NO: 1 or SEQ ID NO: 2 or a fragment of SEQ ID NO: 1 or SEQ ID NO: 2 having at least 6 amino acids;
      ii) a peptide that comprises at least six consecutive amino acids from peptide SEQ ID NO: 1 or SEQ ID NO: 2; and
      iii) a peptide having more than 75% homology with the amino acid sequence of SEQ ID NO: 1 or SEQ ID NO: 2;
   said peptide having a molecular weight ranging from 700 to 3,000 Daltons; and a solubility value in a range from 3 to −9; and
   (b) a topical vehicle for administration of the peptide, such that the peptide diffuses through the epidermal barrier of the skin of the subject for local inhibition of TGFβ1 without systemic absorption of the peptide.

2. The method of claim 1, wherein the subject is a mammal with fibrosis and the method comprises treating fibrosis on the skin of the mammal.

3. The method of claim 1, wherein the subject is a mammal whose skin is free of fibrosis and the composition is administered to the skin of the mammal to prevent fibrotic disease.

4. The method of claim 1, wherein the peptide comprises at most 20 amino acids.

5. The method of claim 1, wherein the peptide consists essentially of SEQ ID NO: 1.

6. The method of claim 1, wherein the peptide consists essentially of SEQ ID NO: 2.

7. The method of claim 1, wherein the subject is a mammal.

8. The method of claim 1, wherein the subject is a human.

9. The method of claim 1, wherein the composition is an emulsion comprising an aqueous phase and a lipophilic phase, wherein the aqueous phase comprises said peptide.

10. The method of claim 9, wherein the aqueous phase also comprises dimethyl sulfoxide.

11. A composition for topical application to skin of a subject, said composition consisting of an emulsion comprising
   (a) an aqueous phase which comprises a peptide that inhibits TBFβ1, said peptide being selected from the group consisting of
      i) SEQ ID NO: 1 or SEQ ID NO: 2 or a fragment of SEQ ID NO: 1 or SEQ ID NO: 2 having at least 6 amino acids;
      ii) a peptide that comprises at least six consecutive amino acids from SEQ ID NO: 1 or SEQ ID NO: 2; and
      iii) a peptide having more than 75% homology with the amino acid sequence of SEQ ID NO: 1 or SEQ ID NO: 2;
   said peptide having a molecular weight ranging from 700 to 3,000 Daltons and a solubility value in a range from 3 to −9, said peptide being present in the composition in an amount capable of reducing fibrosis on the skin of the subject; and
   (b) a lipophilic phase; the emulsion being such that the peptide is absorbed through the epidermal barrier of the skin of the subject for local inhibition of TGFβ1 without systemic absorption of the peptide.

12. The composition of claim 11, wherein the aqueous phase also comprises dimethyl sulfoxide.

13. The composition of claim 1, wherein the composition further comprises an emulsifier.

14. A method for preventing or treating a fibrotic disease or complications thereof on the skin of a subject comprising topically applying to the skin of the subject a composition comprising (a) a peptide that inhibits TGFβ1, said peptide having a molecular weight ranging from 700 to 3,000 Daltons; and a solubility value in a range from 3 to −9; and (b) a topical vehicle for administration of the peptide, such that the peptide diffuses through the epidermal barrier of the skin of the subject for local inhibition of TGFβ1 without systemic absorption of the peptide, wherein the subject is a mammal and the composition is an emulsion comprising the following components: a plurality of antimicrobial compounds in an amount of about 0.01 to 1.0 wt %, a silicone in an amount of about 0.5 to 30 wt %, a mineral oil in an amount of about 1 to 45 wt %. an organic solvent in an amount of about 0.1 to 5 wt %, water in an amount of at least about 40 wt %, a viscosity increasing agent in an amount of about 0.5 to 50 wt %, an emulsifier in an amount of about 0.1 to 3% w/v, and the peptide that inhibits TGFβ1 in an amount of about 0.00 1 to 0.035 wt %:

wherein the components are present in the emulsion in respective amounts such that the peptide diffuses through the epidermal barrier of the skin of the mammal for local inhibition of TGFβ1 without systemic absorption of the peptide, said emulsion being stable at room temperature for more than 24 hours, and wherein the peptide consists essentially of SEQ ID NO: 2, the silicone is a dimethicone, the mineral oil is liquid paraffin, the plurality of antimicrobial compounds comprise methylparaben and propylparaben, the organic solvent comprises dimethylsulphoxide and the viscosity increasing agent comprises cetostearylic alcohol.

* * * * *